United States Patent
Widhalm (10) Patent No.: US 9,279,755 B2
(45) Date of Patent: Mar. 8, 2016

(54) TESTING METHODS AND PASS/FAIL CRITERIA FOR ELECTRIC JOINTS

(75) Inventor: Humi Widhalm, Northville, MI (US)

(73) Assignee: FORD GLOBAL TECHNOLOGIES, LLC, Dearborn, MI (US)

( * ) Notice: Subject to any disclaimer, the term of this patent is extended or adjusted under 35 U.S.C. 154(b) by 1068 days.

(21) Appl. No.: 13/353,838

(22) Filed: Jan. 19, 2012

(65) Prior Publication Data

US 2013/0187658 A1    Jul. 25, 2013

(51) Int. Cl.
| | |
|---|---|
| G01N 3/00 | (2006.01) |
| G01L 1/22 | (2006.01) |
| G01N 3/32 | (2006.01) |
| G01R 31/36 | (2006.01) |
| G01R 31/04 | (2006.01) |

(52) U.S. Cl.
CPC .............. *G01N 3/32* (2013.01); *G01R 31/3627* (2013.01); *G01N 2203/0008* (2013.01); *G01N 2203/0016* (2013.01); *G01N 2203/0617* (2013.01); *G01R 31/04* (2013.01)

(58) Field of Classification Search
CPC ............ H01M 2/1077; H01M 10/613; H01M 10/0525; H01M 2/24; H01M 10/6561; H01M 10/6566; H01M 2/206; H01M 10/441; H01M 10/4207; Y02T 10/7011; G01N 3/00; G01N 2203/0617; G01N 2203/0008; G01N 2203/0016; G01N 3/32; G01R 31/3627; G01R 31/04; G01R 31/3648; G01R 31/025; G01R 31/362; G01R 31/36; G01R 27/14; B23K 31/125

USPC .............. 73/826, 788; 340/650; 324/434, 522
See application file for complete search history.

(56) References Cited

U.S. PATENT DOCUMENTS

| | | | |
|---|---|---|---|
| 3,916,304 A | 10/1975 | Reemer et al. | |
| 6,168,470 B1 | 1/2001 | Ikeda et al. | |
| 6,520,018 B1 | 2/2003 | Flores-Lira | |
| 7,545,147 B2 | 6/2009 | Hart et al. | |
| 7,977,949 B2 | 7/2011 | Williams | |
| 8,450,644 B2* | 5/2013 | Tang et al. | 219/124.1 |
| 2011/0108181 A1* | 5/2011 | Cai et al. | 156/64 |
| 2011/0186204 A1* | 8/2011 | Cai et al. | 156/73.1 |
| 2011/0195302 A1* | 8/2011 | Bucchi | H01M 2/0212 429/179 |
| 2012/0290228 A1* | 11/2012 | Lev | G01N 27/041 702/58 |

FOREIGN PATENT DOCUMENTS

JP      2007059329 A      3/2007

* cited by examiner

*Primary Examiner* — Lisa Caputo
*Assistant Examiner* — Brandi N Hopkins
(74) *Attorney, Agent, or Firm* — David B. Kelley; Brooks Kushman P.C.

(57) ABSTRACT

In one embodiment, a method of evaluating a battery module includes: applying a tension load to a test coupon, the test coupon including a segment of a battery terminal connected to a segment of an interconnector busbar; and measuring electrical resistance across the segments of the test coupon. In certain instances, the method further includes applying a different, second tension load to the segments of the test coupon and repeating the measuring of electrical resistance. In certain other instances, the method further includes forming a plot between various values of electrical resistance as a function of various tension loads.

20 Claims, 5 Drawing Sheets

TESTING METHODS AND PASS/FAIL CRITERIA FOR ELECTRIC JOINTS

TECHNICAL FIELD

The present invention relates to testing methods and Pass/Fail criteria for electric joints.

BACKGROUND

Electric joints are widely used in electric systems such as modules, sensors and switches. In electric vehicles (EV), high-voltage (HV) battery packs include a number of battery modules. Each battery module is assembled from a series of battery cells which are mechanically integrated and electrically interconnected via joints between battery cell terminals and interconnector busbars.

It is desirable to verify and validate the electric joints in order to ensure functionality and durability. Therefore, testing methods are desirable for correlating the joints' integrity to their functionality and durability. In addition, Pass/Fail criteria are also desirable for determining the acceptance of the electric joints.

SUMMARY

In one embodiment, a method of evaluating a battery module includes: applying a tension load to a test coupon, the test coupon including a segment of a battery terminal connected to a segment of an interconnector busbar; and measuring electrical resistance across the segments of the test coupon. In certain instances, the method further includes applying a different, second tension load to the segments of the test coupon and repeating the measuring of electrical resistance. In certain other instances, the method further includes forming a plot between various values of electrical resistance as a function of various tension loads.

In another embodiment, the method further includes forming the test coupon with the battery terminal in a lap sheer configuration relative to the interconnector busbar. In certain instances, the method further includes forming the test coupon with the battery terminal in a coach peel configuration relative to the interconnector busbar. In certain other instances, the method further includes forming the test coupon with the interconnector busbar disposed between and configured in a coach peel configuration relative to first and second battery terminals. In certain other instances, the method further includes forming the test coupon with two battery terminals connected to the interconnector busbar. In certain other instances, the method further includes forming the test coupon with three battery terminals connected to the interconnector busbar. In certain other instances, the method further includes forming the test coupon the battery terminal ultrasonically welded to the interconnector busbar.

DETAILED DESCRIPTION

As required, detailed embodiments of the present invention are disclosed herein. However, it is to be understood that the disclosed embodiments are merely exemplary of the invention that may be embodied in various and alternative forms. Therefore, specific structural and functional details disclosed herein are not to be interpreted as limiting, but merely as a representative basis for the claims and/or a representative basis for teaching one skilled in the art to variously employ the present invention.

Moreover, except where otherwise expressly indicated, all numerical quantities in the description and in the claims are to be understood as modified by the word "about" in describing the broader scope of this invention. Also, unless expressly stated to the contrary, the description of a group or class of material being suitable or preferred for a given purpose in connection with the invention implies that mixtures of any two or more members of the group or class may be equally suitable or preferred.

In terms of the functionality or electric requirements of the joints, the joints are to enable the interconnection among battery cells with lowest interfacial resistances across them and to ensure such interconnection during service by providing not only adequate initial or beginning of life (BOL) strength but also sufficient end of life (EOL) strength. In this connection, the BOL and EOL values can be indicative of joint strength. Therefore, the maximum possible load must be no greater than the BOL and EOL values of a particular joint.

The BOL and EOL strengths may depend on base metal strengths including those for battery cell terminals and ICB busbars, and/or electric characteristics such as low interfacial resistance across the joints, which is in-turn affected by joint strength. On the other hand, the BOL and EOL strengths of a joint must be higher than the maximum loads on the joint at the respective times.

Without wanting to be limited to any particular theory, it is believed that lower electric resistance across the joints is desirable since it generates relatively lower power loss across the joints and hence less heat buildup around the joints during operation.

In one or more embodiments, the term "joint(s)" or "electric joint(s)" refers to a connection between two or more components of any materials or conductive materials. One joint may include one, two, three or more welds or nuggets. In certain instances, electric joints are on coupon samples resembling actual joints in actual products. In certain other instances, electric joints are directly cut from the actual products such as battery modules. Battery modules include electric joints between one or more battery cell terminals and one interconnector busbar.

The minimum BOL peak loads are the lower limits below which weld integrity would be compromised. Hence, the minimum BOL peak loads set the lowest thresholds for joint strength. The optimum BOL peak loads are the peak loads at which the electric resistance across the joints is at the minimal for the respective combinations of the materials of battery cell terminals and ICB busbars. Since the optimum BOL peak loads are higher than the minimum BOL peak loads, achieving the optimum BOL peak loads ensures the satisfaction of the minimum BOL peak loads. Achieving the optimum BOL peak loads is desirable and it is desirable to produce the lowest electric resistances across the joints. Many other factors, however, need to be considered in order to optimize the entire system and manufacturing process. For example, attaining the optimum BOL peak loads may shorten the life of joining tools and increase the rework rate of the joints and the maintenance frequency of the joining tools due to buildup and sticking on the tool surfaces, i.e., accelerated adhesive wear. Nevertheless, achieving the optimum BOL peak loads or even higher peak loads may be desirable for certain combinations of the materials in battery cell terminals and ICB busbars in order to avoid pulling open of weld(s) by the joining tool.

Now with reference to testing methods, it is desirable to know the strength and fatigue limits for joined components. The joints have two potential modes of exceeding limitations. Particularly, on the joints between battery cell terminals and ICB busbars in battery modules, there can be two potential modes of exceeding component limitations due to different types of loads: shearing and peeling loads. Hence, testing methods that simulate these loading conditions and evaluate potential failure mechanisms are desired. In addition, it would be beneficial to have Pass/Fail criteria based on component limitations.

The Pass/Fail criteria, according to one or more embodiments of the present invention, help prevent defective joints from being passed along to downstream manufacturing processed and/or from escaping to end users. In particular, the Pass/Fail criteria help prevent potential failure modes or effects from occurring.

Testing methods and Pass/Fail criteria, according to one or more embodiments of the present invention, can be applicable to welded coupons and actual modules. These testing methods can be used for research and development of welding materials, processes and tooling, as well as daily startups, auditing and screening during mass production.

On another point, it is also desirable to obtain measurements related to electrical resistance across joined battery components. Generally speaking, lower interfacial resistance across the joints generates lower power loss and less heat buildup around the joints. There is also a need to have a target electric requirement for the joints between battery cell terminals and ICB busbars in battery modules of HV battery packs for EV applications.

Furthermore, it is desirable to have clear information on component fatigue under various conditions. For example, excessive vibration can cause the joints to see additional loading. Hence, testing methods and Pass/Fail criteria are desirable to address potential modes of exceeding component limitations due to fatigue.

The present invention, in one or more embodiments, is advantageous in providing methods for strength testing battery modules, particularly joints formed between battery terminals and interconnector busbars to address potential modes of exceeding component limitations, effects, and correlate to the functionality and life cycle of joined battery components. Samples can be taken from actual modules as a periodic control measure, e.g., during daily startup and shut-down procedures in a manufacturing facility.

The present invention, in one or more embodiments, is advantageous in enabling correlation to other electromechanical component features, e.g., electric resistance across the joints between battery cell terminals and ICB busbars. Correlative data can then be mathematically derived without the need for further testing. The use of these tests offers greater flexibility and cost-advantages. In addition, BOL Pass/Fail criteria for the joints between battery cell terminals and ICB busbars can also be derived from the identification of these relationships as well. For example, minimum electric resistance and maximum electric resistance have been identified for the joints.

In one embodiment, testing methods include static testing and dynamic testing, namely, tensile testing and fatigue testing, for evaluating the strengths and durability of electric joints, respectively. These testing methods are best suitable for development of joint materials, joint designs, and joining processes and tooling. The tensile testing is short and hence a good choice for routine evaluations such as daily startup and close down processes and auditing/screening during mass production, whereas the fatigue testing is lengthy and thus mainly used for design and development.

In another embodiment, the testing methods include analyzing potential failure modes resulted from potential loads on electric joints during service and dividing the potential loads into two primary categories, namely, shear loads and peel loads. Due to these two potential loads, two potential failure modes may occur on electric joints, namely shear fracture and bend fracture. Accordingly, testing coupon samples are invented herein to simulate these two potential load conditions and evaluate the joint strengths and durability under these potential failure mechanisms, including lap-shear coupon samples and coach-peel coupon samples.

Figure 1:
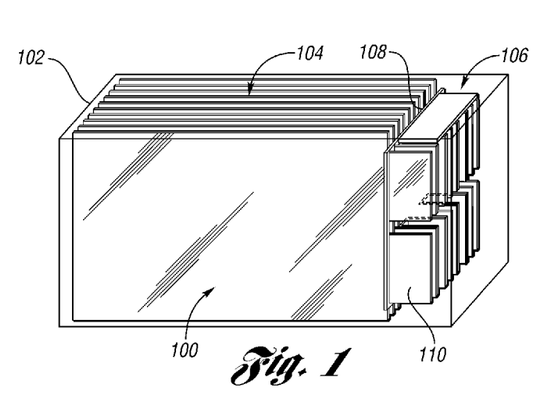
FIG. 1 schematically depicts a battery module in a perspective view.

FIG. 1 schematically depicts a non-limiting example of battery cell stack within a battery module 100 in a perspective view. The packaging geometry for the battery module 100 is shown at 102. The battery module 100 includes a series of battery cells 104. Each battery cell 104 includes two terminals 106. The battery cell terminals 106 are arranged in a predetermined pattern to align with an interconnector board (ICB) 108. The ICB 108 includes several interconnector busbars 110 to which the battery cell terminals 106 are joined via any suitable methods including ultrasonic welding (USW). Each joint has one or more welds joining one or more battery cell terminals and one interconnector busbar at the location where they mate and overlap. The interconnector busbars 110 are pre-joined mechanically and metallurgically to the ICB 108 which is attached to the structural frame of the battery module. Thus, the electric joints in battery modules are exposed to shear loads and peel loads during service.

In yet another embodiment, the testing methods further include creating coupon samples with lap-shear joints and coach-peel joints, respectively, and real product samples such as double coach-peel joints from real battery modules. The lap-shear coupon samples and coach-peel coupon samples allow application of the shear loads and peel loads, respectively, from a single tensile tester or a single fatigue tester, and thus address the potential failure effects caused by the potential service load conditions.

For creating a lap-shear coupon sample, coupons are cut from a sheet or a foil of component materials. The coupons are then mated/overlapped at the ends and joined using any suitable methods such as USW, as shown schematically in FIGS. 2A and 2B.

Figure 2A:
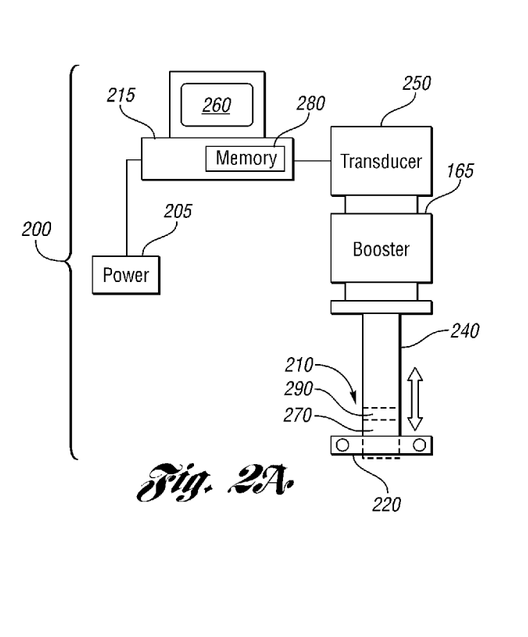
FIG. 2A schematically depicts a front view of a system for joining battery components in a lap shear configuration.
Figure 2B:
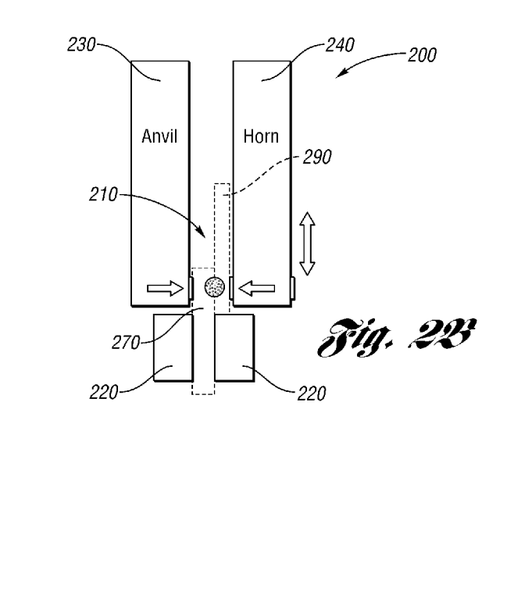
FIG. 2B schematically depicts a side view of the system of FIG. 2A.

FIG. 2A schematically depicts a front view of an exemplary joining system for creating joints in a lap-shear configuration. FIG. 2B schematically depicts a side view of the system of FIG. 2A. The joining system 200 consists of a power supply 205, a controller 215 with a display 260, a transducer 250, a booster 265, a horn 240 and a clamping fixture 220. The power supply 205 supplies high frequency electric signals to the transducer 250 as controlled by the controller 215. The transducer 250 converts the high frequency electric signals to high frequency mechanical vibrations. The booster 265 is tuned to vibrate at a required high frequency to increase, or decrease, or maintain the amplitude of the vibrations, and couples the transducer 250 with the horn 240. The horn 240 grips the surface of the coupon sample 210 and vibrates at high frequency to join coupon materials 270 and 290. Thicker coupon 270 is clamped by the fixture 220, whereas thinner coupons 290 are supported by the fixture 220. During the high frequency vibrations, a static force is applied from the horn 240 onto the coupons 290 along the direction perpendicular to the vibration direction, while the coupon 270 is gripped by a stationary anvil 230.

Figure 3A:
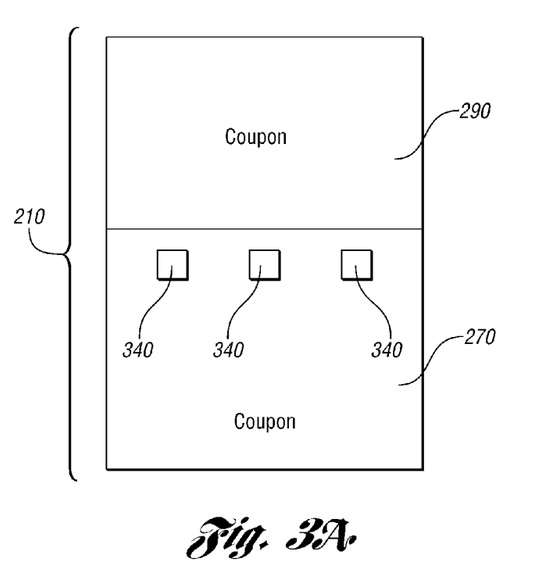
FIG. 3A schematically depicts a front view of a battery test coupon in lap shear configuration.
Figure 3B:
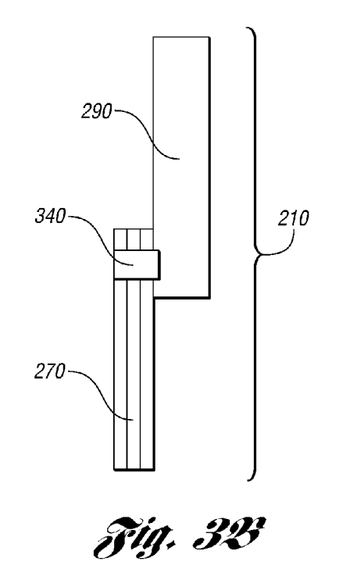
FIG. 3B schematically depicts a side view of the battery test coupon of FIG. 3A.

FIGS. 3A and 3B schematically depict enlarged front and side views of the lap-shear coupon sample 210 referenced in FIGS. 2A and 2B. The coupon sample 210 includes a joint between the coupon materials 270 and 290. The joint has 3 welds 340 which connect the coupon materials 270 and 290. The coupon materials 270 and 290 may be a single layer or multiple layers of sheets or foils, respectively. In certain instances, the coupon 270 may be a single layer from a sheet of high purity copper as used for interconnector busbars, whereas the coupons 290 may be multiple layers from foils of high purity copper or aluminum as used for battery cell terminals. More or fewer layers of foils may be used for the coupons 290 to test varied conditions as well, with an exemplary test set up shown schematically in FIG. 4.

For creating a coach-peel coupon sample, coupons are cut from a sheet or a foil of component materials, and bent by 90 degrees at one end. The coupons are then mated at the bent ends and joined using any suitable methods such as USW, as shown schematically in FIGS. 5A and 5B.

Figure 5A:
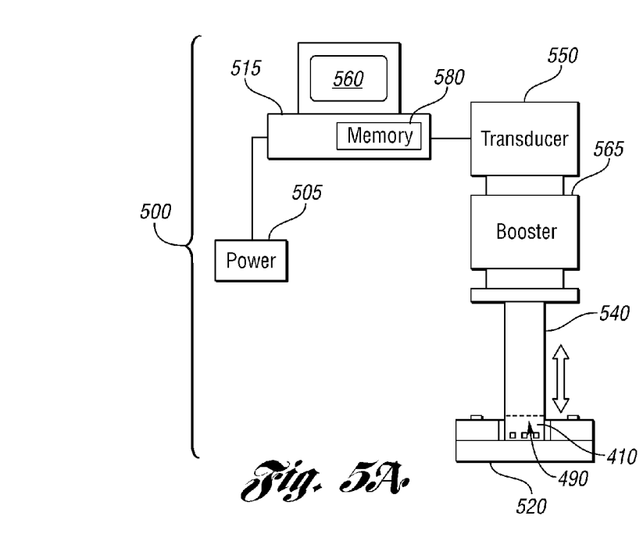
FIG. 5A schematically depicts a front view of a test machine for joining battery components in a coach peel configuration.
Figure 5B:
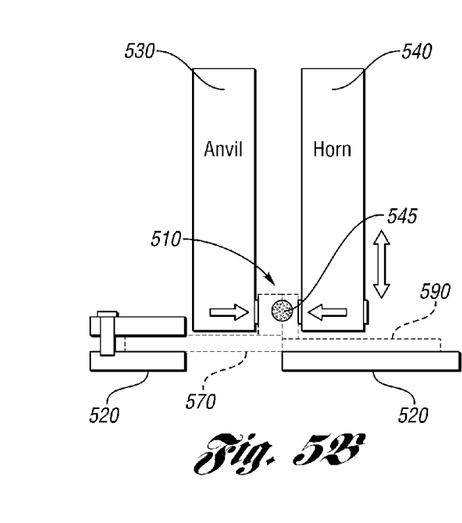
FIG. 5B schematically depicts a side view of a testing machine for joining battery components in a coach peel configuration.

FIG. 5A schematically depicts a front view of an exemplary joining system for creating joints in a coach-peel configuration. FIG. 5B schematically depicts a side view of the system of FIG. 5A. The joining system 500 consists of a power supply 505, a controller 515 with a display 560, a transducer 550, a booster 565, a horn 540 and a clamping fixture 520. The power supply 505 supplies high frequency electric signals to the transducer 550 as controlled by the controller 515. The transducer 550 converts the high frequency electric signals to high frequency mechanical vibrations. The booster 565 is tuned to vibrate at a required high frequency to increase, or decrease, or maintain the amplitude of the vibrations, and couples the transducer 550 with the horn 540. The horn 540 grips the surface of the coupon sample 510 and vibrates at high frequency to join coupon materials 570 and 590. Thicker coupon 570 is clamped by the fixture 520, whereas thinner coupons 590 are supported by the fixture 520. During the high frequency vibrations, a static force is applied from the horn 540 onto the coupons 590 along the direction perpendicular to the vibration direction, while a stationary anvil 530 grips the coupon 570.

Figure 6A:
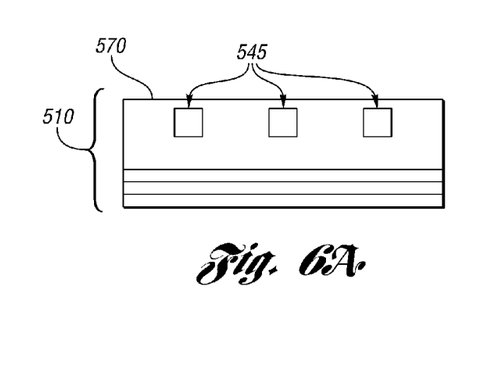
FIG. 6A schematically depicts a front view of a battery test coupon in a coach peel configuration.
Figure 6B:
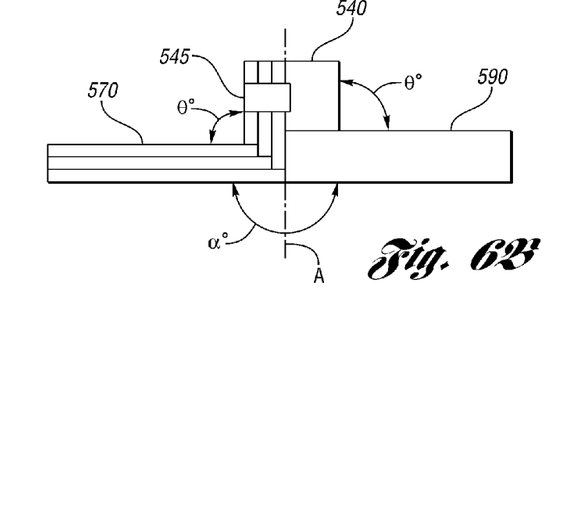
FIG. 6B schematically depicts a side view of a battery test coupon.

FIGS. 6A and 6B schematically depict enlarged front and side views of the coach-peel coupon sample 510 referenced in FIGS. 5A and 5B. The coupon sample 510 includes a joint between the coupon materials 570 and 590. The joint has three welds 545 which connect the coupon materials 570 and 590. The coupon materials 570 and 590 may be a single layer or multiple layers of sheets or foils, respectively. In certain instances, the coupon 570 may be a single layer from a sheet of high purity copper as used for interconnector busbars, whereas the coupons 590 may be multiple layers from foils of high purity copper or aluminum as used for battery cell terminals. More or fewer layers of foils may be used for the coupons 590 to test varied conditions as well.

Coupon samples may be prepared from flat or bent sheets or foils of component materials in the configurations including 1-layer sheet/foil with 1-layer sheet, 2-layers of sheets/foils with 1-layer sheet, 3-layers of sheets/foils with 1-layer sheet, or multiple layers of foils with 1-layer sheet/foil, for lap-shear joints and coach-peel joints, respectively. While the illustrated coupon samples include joints having three welds per joint, other coupon samples may be created using the methods disclosed herein with more or fewer welds than three. Moreover, coupons may be joined using any suitable methods, including USW, laser welding, resistance spot welding, brazing, fastening, clinching, crimping and soldering. The application of the testing methods and systems disclosed herein can be translated to samples joined by any joining methods.

Figure 7:
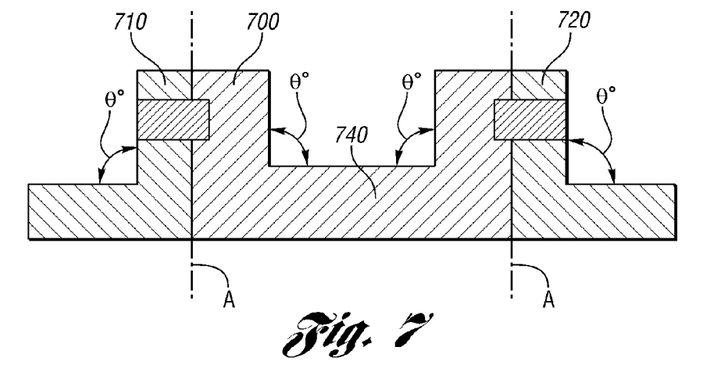
FIG. 7 schematically depicts a cross-sectional view of an exemplary battery test coupon.

For creating a double coach-peel sample from a real battery module, the sample is sectioned off from the real battery module. FIG. 7 schematically depicts a cross-sectional view of double coach-peel joints cut from a real battery module, where one joint is formed between battery cell terminals 710 and one side of an interconnector busbar 700, and the other joint between battery cell terminals 720 and the other side of the interconnector busbar 700. The sectioning and shaping processes include the following steps: (i) The battery cell terminals 710 and 720 are sectioned off from the battery cells along the connection to the cell tabs near the cell pouch edge (in case of laminated cells) to generate sufficient length on the free ends of the battery cell terminals; (ii) The interconnector busbar U-channel 700 is cut off from the interconnector busbar; and (iii) The free ends of the battery cell terminals are bent outwards by 90 degrees to align with the base of the U-channel, forming the real battery module sample with the double coach-peel joints.

In yet another embodiment, the static testing method includes applying static loads to the joints on coupon samples or real battery module samples, respectively, recording the maximum loads, termed "peak loads", at which joint fracture starts during the static testing, and using the peak loads as a measure of joint strengths. If the static testing is conducted before any sample aging, the peak loads are regarded as BOL joint strengths.

Figure 4:
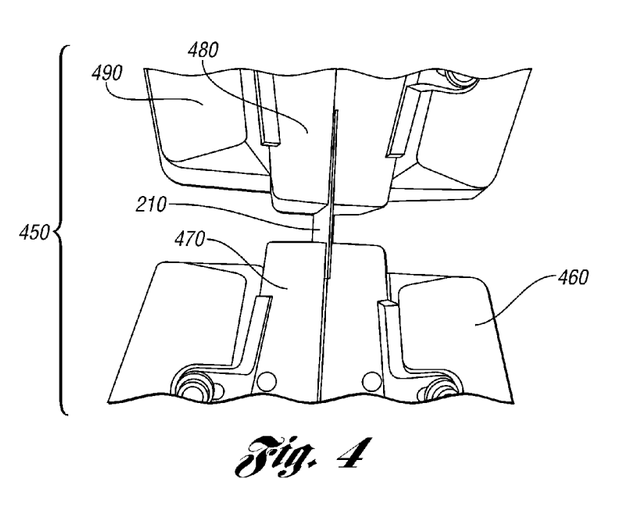
FIG. 4 schematically depicts a side view of a testing system.

FIG. 4 schematically depicts a partial view of a testing system 450 for testing the lap-shear coupon sample 210 referenced in FIGS. 2A, 2B, 3A and 3B. The system 450 includes a lower and upper fixture 460 and 490 which adapt the lower and upper grip 470 and 480, respectively. The lower fixture 460 is stationary, whereas the upper fixture 490 can move vertically upwards. The static testing or tensile testing method includes the following steps: (i) the lap-shear coupon sample 210 is loaded into the grips 470 and 480 of a tensile tester which may be also referred to as a tensile frame or tensile machine; (ii) a tension is applied to the sample 210 by moving the upper grip 480 upwards at a speed of about 10 mm/min; and (iii) with increasing tension, the sample 210 deforms or elongates along the load direction. A maximum tension is eventually attained when a micro-crack or shear fracture initiates in one or more welds on the sample 210. This maximum tension is termed peak load. Thereafter, the crack grows and/or shear fracture develops while the tension reduces. The testing may be stopped and the peak load recorded for the individual sample 210. Lastly, the post-test sample is examined.

The static testing method for coach-peel coupon samples and real battery module samples is identical to that disclosed herein for lap-shear coupon samples. However, the peak loads are different due to different failure mechanisms resulted from the different layouts of these samples. Coach-peel joints fail normally at lower peak loads than lap-shear joints, yet a correlation of the peak loads, typically a proportional relation, can be established between the two different types of joints. In double coach-peel samples cut from real battery modules, the weaker side fails first. For instance, the joint with two-layers of battery cell terminals fails normally before the other joint with three-layers of battery cell terminals.

In yet another embodiment, the dynamic testing method includes applying cyclic loads to the joints on coupon samples or real battery module samples, respectively, and recording the number of cycles the joints experience. At a pre-determined number of cycles corresponding to a required fatigue life, stopping the cyclic loads, measuring electric resistances across the joints, conducting static testing, recording the peak loads at which joint fracture starts during this subsequent static testing, and using the peak loads as a measure of EOL joint strengths. The EOL peak loads are then correlated to BOL peak loads using the joints created from the same materials, same geometry, same number and size of welds per joint, same joining method, and same joining parameters.

A fatigue tester is essentially same as the tensile tester except that the fatigue tester is capable of and rated for applying cyclic loads at designated frequencies. Therefore, a fatigue tester can be used for both dynamic (fatigue) and static (tensile) testing, whereas a tensile tester can be used only for static (tensile) testing. The dynamic testing or fatigue testing method is similar to the static testing or tensile testing method except that the dynamic testing method requires specifications for the max load and frequency of the cyclic loads, and ratio R.

In the present invention, the dynamic testing or fatigue testing method includes the following specifications: (i) the max load of the cyclic loads is about 100 N which is 40% above the average load, 60 N, on a 3-weld joint at 10 G acceleration and varies with the mass of a real product such as a real battery module; (ii) the ratio R is about 0.1; and (iii) the frequency of the cyclic loads is about 70 Hz to 100 Hz. Furthermore, five million cycles are considered to be the number of cycles corresponding to EOL, namely the criterion of reaching EOL.

In yet another embodiment, the testing methods further include measuring electric resistances across electric joints prior to any testing, conducting static testing and measuring BOL peak loads, and verifying and validating the electric joints by comparing the measured BOL peak loads to mechanical Pass/Fail criteria.

In yet another embodiment, methods for deriving mechanical Pass/Fail criteria and mechanical guidelines include determining minimum BOL peak loads according to functionality and durability requirements, and establishing optimum BOL peak loads and maximum achievable peak loads according to electrical-mechanical relations and base materials properties, respectively. Pass/Fail criteria are needed to prevent the potential failure modes and effects from occurring during service.

In terms of the functionality requirements, electric joints are to enable the interconnection among the components, such as battery cell terminals, with lowest interfacial resistances. In terms of the durability requirements, electric joints are to ensure such interconnection against fatigue degradation during service by providing not only adequate initial or BOL joint strengths but also sufficient EOL joint strengths. The adequate BOL joint strengths which ensure sufficient EOL joint strengths set the minimum BOL joint strengths, whereas the BOL joint strengths which lead to the lowest interfacial resistances set the optimum BOL joint strengths. Obviously, both the minimum and optimum BOL joint strengths cannot exceed the inherent limits of base materials of joined components, namely maximum achievable joint strengths.

The maximum achievable joint strengths depend on the strengths of base materials of joined components, for instance, battery cell terminals' materials. Basically, the peak loads of the base materials may be considered as the maximum achievable peak loads of the joints since the base materials would have failed earlier than the joints when the actual loads on the joints would have exceeded the peak loads of the base materials. Accordingly, the maximum achievable peak loads of the joints are calculated based on the number of layers, width, thickness and ultimate tensile strengths (UTS) of the base materials. For lap-shear joints, the maximum achievable peak load is calculated using the following equation:

$$\text{maximum achievable peak load} = \text{number of layers} \times \text{width} \times \text{thickness} \times \text{UTS}$$

The minimum BOL peak loads are the lower limits below which joint integrity, functionality and durability would be compromised. Hence, the minimum BOL peak loads set the lowest thresholds for joint strengths. The optimum BOL peak loads are the peak loads at which the electric resistances across the joints are at the minimum for the respective combinations of component materials such as battery cell terminals and interconnector busbars.

The minimum BOL peak loads are determined herein to meet or exceed both functionality requirements and durability requirements, whichever are higher. The higher peak loads are then adopted as the ultimate minimum BOL peak loads in the mechanical Pass/Fail criteria.

For determining the minimum BOL peak loads meeting or exceeding the functionality requirements, the method includes the following steps: (i) Creating coupon samples with lap-shear joints using various process parameters which produce different joint strengths and thus different electric resistances across the joints; (ii) Measuring the electric resistances across the joints using the non-destructive evaluation (NDE) methods for electric joints invented by the present inventor and disclosed elsewhere; (iii) Conducting the static testing on the same joints, and measuring the peak loads of the joints; (iv) Correlating the mean electric resistances to the mean peak loads, and quantifying the electrical-mechanical relation using the regression method invented by the present inventor and disclosed elsewhere; The mean electric resistances vary with the mean peak loads; A lower mean peak load corresponds to a higher mean electric resistance; With increasing mean peak loads, the mean electric resistances decrease monotonically until a minimum is attained; (v) Locating the mean peak load at which the mean electric resistance meets the electric Pass criterion invented by the present inventor and disclosed elsewhere, and recording this mean peak load as the minimum BOL peak load for the joints of the same materials, same geometry, and same number and size of welds per joint; (vi) Locating the mean peak load at which the mean electric resistance is at the minimum, and recording this mean peak load as the optimum BOL peak load for the joints. Thus, the method establishes the minimum BOL joint strengths meeting or exceeding the functionality requirements and the optimum BOL joint strengths.

For determining the minimum BOL peak loads meeting or exceeding the durability requirements, the method includes the following steps: (i) Since the functionality requirements on electric joints at EOL are the same as at BOL, the electric properties such as electric resistances at EOL are required to be the same as at BOL. Hence, the threshold for satisfactory EOL electric resistances is deducted from the electric Pass/Fail criteria invented by the present inventor and disclosed elsewhere; (ii) This threshold for the satisfactory EOL electric resistances is correlated to the satisfactory EOL peak load using individual measurements or the regression method invented by the present inventor and disclosed elsewhere; (iii) By conducting fatigue testing, the satisfactory EOL peak load is in-turn correlated to the satisfactory BOL peak load for the joints of the same materials, same geometry and same design. Thus, the method establishes the minimum BOL joint strengths meeting or exceeding the durability requirements.

Since the optimum BOL peak loads are higher than the minimum BOL peak loads, achieving the optimum BOL peak loads ensures the satisfaction of the minimum BOL peak loads. Achieving the optimum BOL peak loads is desirable for producing the lowest electric resistances across the joints. Many other factors, however, need to be considered in order to optimize the entire system and manufacturing process. For example, attaining the optimum BOL peak loads may shorten the life of joining tools and increase the rework rate of the joints and the maintenance frequency of the joining tools due to buildup and sticking on the tool surfaces, i.e., accelerated adhesive wear. Nevertheless, achieving the optimum BOL peak loads or even higher peak loads may be desirable for certain combinations of the materials of battery cell terminals and interconnector busbars in order to avoid pulling open of weld(s) by the joining tools, if the tool surface condition is not optimized or maintained due to other constraints, or if the controller of a joining equipment does not provide the function for timing optimization. Obviously, this is not a functionality or durability requirement but a manufacturing necessity.

In yet another embodiment, mechanical Pass/Fail criteria include the minimum BOL peak loads, and mechanical guidelines include optimum BOL peak loads and maximum achievable peak loads. The minimum BOL peak loads set the criteria above which electric joints are considered satisfactory in terms of their functionality and durability. The optimum BOL peak loads set the thresholds at which the electric resistances across electric joints are lowest. The maximum achievable peak loads denote the inherent limits that any joints cannot exceed. These peak loads depend on many factors, including the base materials strengths and geometry of joined components, number and size of welds per joint, and joining method.

EXAMPLE

Example 1

Table 1 lists the maximum achievable peak loads for lap-shear joints calculated using the following equation:

maximum achievable peak load=number of layers× width×thickness×UTS where the base materials are the materials for battery cell terminals, namely copper and aluminum foils of 45 mm in width and 0.2 mm in thickness. In this example and throughout the embodiments, 3P and 2P stand for three layers and two layers, respectively.

TABLE 1

| Base Metals | UTS (N/mm$^2$) | Battery Cell Terminals | Peak Loads of Base Metals with Cross Section of Entire Battery Cell Terminals (N) |
|---|---|---|---|
| 0.2 mm Cu | 240 | 3P Cu | 6480 |
|  |  | 2P Cu | 4320 |
| 0.2 mm Al | 77 | 3P Al | 2080 |
|  |  | 2P Al | 1390 |

Figure 9:
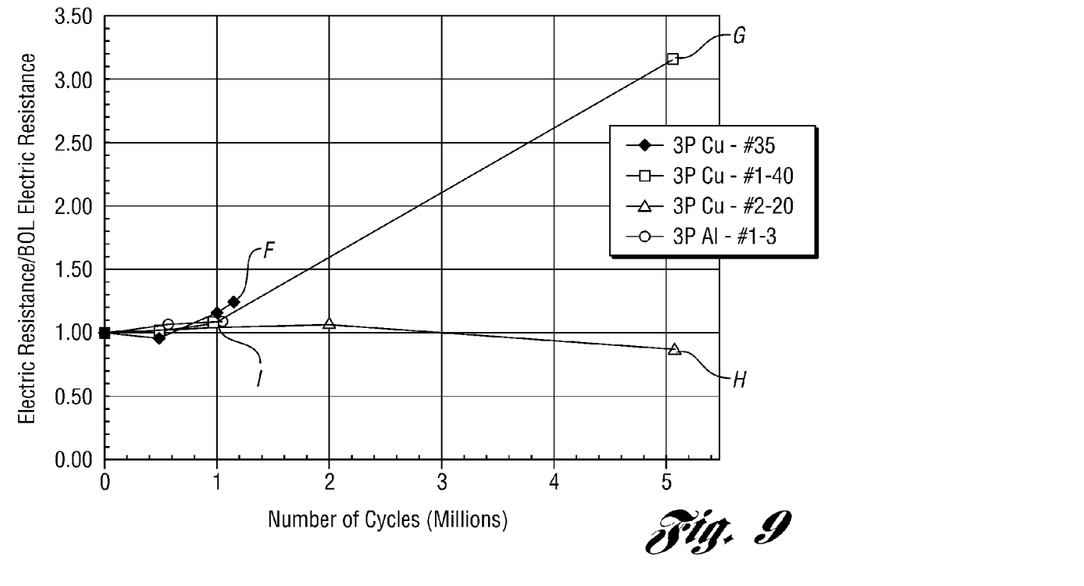
FIG. 9 illustratively depicts a fatigue plot, showing number of cycles versus percentage change in electrical resistance.
Figure 10:
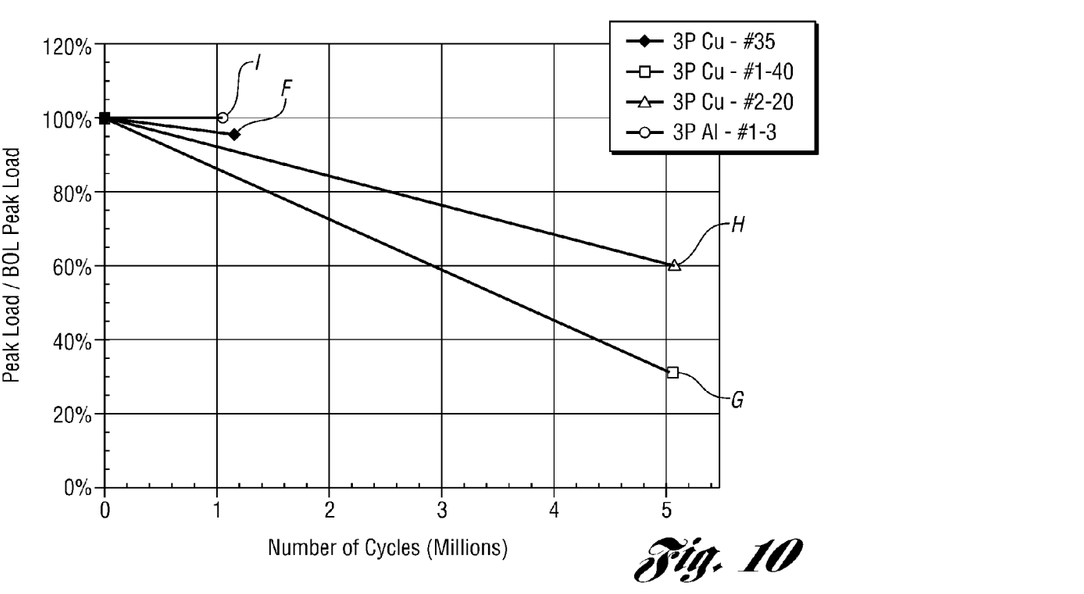
FIG. 10 illustratively depicts a fatigue plot, showing number of cycles versus percentage change in peak load.

Data from the same samples is plotted as shown in FIG. 10. FIG. 10 shows a graph 1000 of peak load for fatigued coupons over beginning of life peak load versus number of cycles for test coupons of different material composition as discussed with respect to FIG. 9. The electrical resistance is measured for several overlapping coupons via repetitive loading. Four test sample groups are measured. For samples F, the end of life peak load is approximately 20% less than the corresponding BOL peak load. For samples I, the end of life peak load is approximately the same as the corresponding BOL peak load. For samples H, the end of life peak load is approximately 40% lower than the corresponding BOL peak load. For samples G, the end of life peak load is approximately 65% lower than the corresponding BOL peak load.

Example 2

The minimum BOL peak loads and optimum BOL peak loads meeting or exceeding the functionality requirements are derived using the method in one or more embodiments of the present invention, as summarized in Table 2.

In this example, the base materials are the materials for battery cell terminals, namely copper and aluminum foils of 45 mm in width and 0.2 mm in thickness, and the lap-shear joints have three welds per joint and each weld is 4 mm in width.

TABLE 2

| Base Metals | Battery Cell Terminals | Minimum BOL Peak Loads (N) | Optimum BOL Peak Loads (N) |
|---|---|---|---|
| 0.2 mm Cu | 3P Cu | 990 | 1705 |
|  | 2P Cu | 674 | 1395 |
| 0.2 mm Al | 3P Al | 515 | 1160 |
|  | 2P Al | 343 | 775 |

Example 3

Dynamic testing or fatigue testing is conducted on lap-shear joints using a fatigue tester under the following conditions: (i) the max load of the cyclic loads is about 100 N which is 40% above the average load, 60 N, on a 3-weld joint at 10 G acceleration; (ii) the ratio R is about 0.1; and (iii) the frequency of the cyclic loads is about 70 Hz. Five million cycles are considered to be the criterion of reaching EOL.

Electric resistances across the lap-shear joints are measured using the NDE method invented by the present inventor and disclosed elsewhere before and after the fatigue testing, respectively. The electric resistances measured before the fatigue testing are considered as the BOL electric resistances. The electric resistances measured after the fatigue testing are taken as the electric resistances at the given number of fatigue cycles. If the number of fatigue cycles reaches the EOL criterion, the electric resistances measured after the fatigue testing are considered as the EOL electric resistances.

Figure 8:
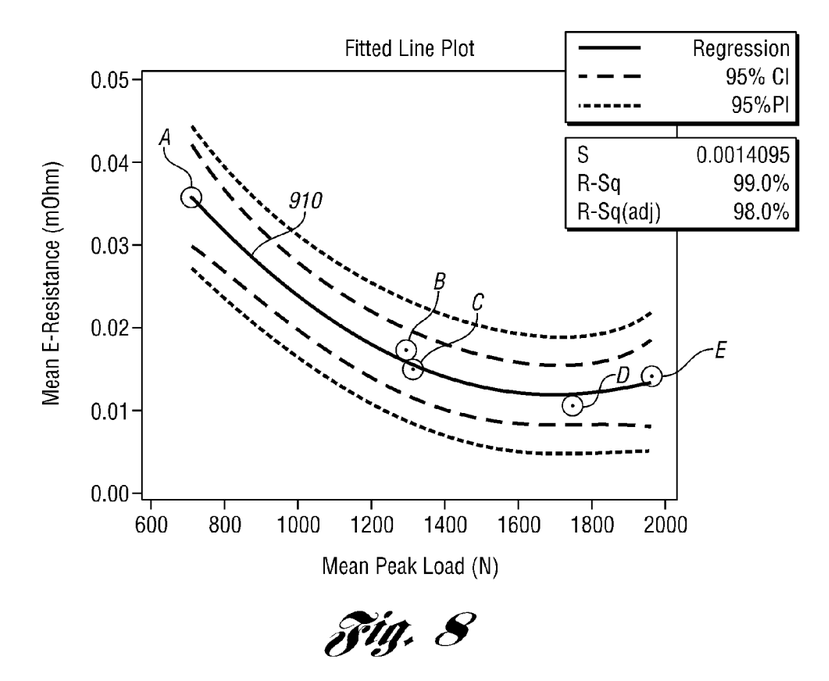
FIG. 8 illustratively depicts values of peak load as a function of values of electrical resistance.

FIG. 8 illustratively shows the change of the electric resistances across the lap-shear joints of different materials with increasing fatigue cycles, where the electric resistances are normalized by the BOL electric resistances of the same joints. Among many lap-shear coupon samples tested, sample F (3P Cu) is tested for over a million cycles after which the electric resistance across the joint is approximately 30% higher than its BOL value; Sample G (3P Cu) is tested for over five million cycles after which the electric resistance across the joint is more than 3-times higher than its BOL value; Sample H (3P Cu) is tested for over five million cycles after which the electric resistance across the joint is slightly lower than its BOL value; and Sample I (3P Al) is tested for over a million cycles after which the electric resistance across the joint is approximately the same as its BOL value. The fatigue degradation rate is the highest with sample G, followed by sample H, and the slowest with sample F. The joint on aluminum (sample I) shows slower degradation since aluminum is much softer than copper, and hence more tolerable to cyclic loads or fatigue in this application.

After the fatigue testing of each lap-shear coupon sample, electric resistance across the lap-shear joint is measured using the NDE method invented by the present inventor and disclosed elsewhere, and then each lap-shear coupon sample is loaded onto a tensile tester for static testing to determine the peak load as a measure of joint strength. FIG. 9 illustratively shows the degradation of joint strengths of different materials with increasing fatigue cycles, where the peak loads are normalized by the BOL peak loads of the joints created with the same conditions, namely the same materials, same geometry, same number and size of welds per joint, same joining method, and same joining parameters. Among the many lap-shear coupon samples tested, the peak load of sample F is reduced by about 5% from the BOL value after over a million cycles; the peak load of sample G is reduced by about 70% from the BOL value after over five million cycles; the peak load of sample H is reduced by about 40% from the BOL value after over five million cycles; and the peak load of sample I remains almost constant after over a million cycles.

In these fatigue testing examples, sample G presents the worst-case-scenario (WCS) with the highest degradation rate and has reached EOL cycles. Accordingly, its electric resistance and peak load measured after over five million cycles are considered as EOL electric resistance and EOL peak load, respectively. Assuming that this EOL electric resistance meets the electric Pass criterion invented by the present inventor and disclosed elsewhere, this EOL peak load is considered satisfactory and then correlated to the BOL peak load of the joints created with the same conditions. This BOL peak load sets the minimum BOL peak load meeting or exceeding the durability requirements for 3P Cu.

For each combination of joint materials, joint geometry, joint design and joining method, the WCS with the highest degradation rate approaching EOL cycles is used to determine the satisfactory EOL peak load, if the corresponding EOL electric resistance meets the electric Pass criterion. Using the fatigue testing results, the satisfactory EOL peak load is then correlated to the BOL peak load which finally sets the minimum BOL peak load meeting or exceeding the durability requirements.

The derived minimum BOL peak loads meeting or exceeding the durability requirements are summarized in Table 3, where the base materials are the materials for battery cell terminals, namely copper and aluminum foils of 45 mm in width and 0.2 mm in thickness, and the lap-shear joints have three welds per joint and each weld is 4 mm in width.

TABLE 3

| Base Metals | Battery Cell Terminals | Minimum BOL Peak Loads (N) |
|---|---|---|
| 0.2 mm Cu | 3P Cu | 1300 |
|  | 2P Cu | 1000 |
| 0.2 mm Al | 3P Al | 560 |
|  | 2P Al | 370 |

Comparing Table 2 to Table 3, the minimum BOL peak loads meeting or exceeding the durability requirements (Table 3) are higher than those meeting or exceeding the functionality requirements (Table 2). Accordingly, the higher minimum BOL peak loads (Table 3) are adopted as the ultimate minimum BOL peak loads in the mechanical Pass/Fail criteria.

Example 4

Table 4 lists the mechanical Pass/Fail criteria and mechanical guidelines derived using the methods in one or more embodiments of the present invention and the measured data in the above examples. In Table 4, mechanical Pass/Fail criteria include the minimum BOL peak loads, and mechanical guidelines include optimum BOL peak loads and maximum achievable peak loads. The minimum BOL peak loads set the criteria above which electric joints are considered satisfactory in terms of their functionality and durability. The optimum BOL peak loads set the thresholds at which the electric resistances across electric joints are lowest, and hence should be used as guidelines for best practice. The maximum achievable peak loads denote the inherent limits that any joints cannot exceed, and thus should be used as guidelines for selecting tensile tester, setting test parameters, and trouble-shooting.

TABLE 4

| Base Metals | Battery Cell Terminals | Mechanical Pass/Fail Criteria Minimum BOL Peak Loads (N) | Guidelines - Best Practice Optimum BOL Peak Loads (N) | Guidelines - Know-the-Limit Maximum BOL Peak Loads (N) |
|---|---|---|---|---|
| 0.2 mm Cu | 3P Cu | 1300 | 1705 | 6480 |
|  | 2P Cu | 1000 | 1395 | 4320 |
| 0.2 mm Al | 3P Al | 560 | 1160 | 2080 |
|  | 2P Al | 370 | 775 | 1390 |

It should be noted that the forces and loads calculated or measured in these examples and throughout the embodiments are based on nominal mechanical properties from the standards or specifications of the battery cell terminals and interconnector busbars and their as-is (incoming) pre-strain conditions. If these properties and pre-strain conditions change, the forces and loads should be calibrated accordingly.

The following application discloses and claims methods and Pass/Fail criteria for electric joints that may be related to the methods disclosed and claimed in the U.S. patent application Ser. No. 13/353,866 which is incorporated herein by reference in its entirety.

While the best mode for carrying out the invention has been described in detail, those familiar with the art to which this invention relates will recognize various alternative designs and embodiments for practicing the invention as defined by the following claims.

What is claimed:

1. A method of evaluating a battery module, comprising:
applying a tension load to a joint of the battery module, the joint including a segment of a battery terminal connected to a segment of an interconnector busbar; and
measuring electrical resistance across the segments of the joint.

2. The method of claim 1, further comprising applying a different, second tension load to the segments of the joint and repeating the measuring of electrical resistance.

3. The method of claim 2, further comprising forming a plot between various values of electrical resistance as a function of various tension loads.

4. The method of claim 3, further comprising comparing measured electrical resistance to the plot and obtain a corresponding tension load to evaluate the battery module.

5. The method of claim 4, further comprising eliminating the joint from being included in the battery module if the corresponding tension load does not meet a set criterion.

6. The method of claim 1, further comprising forming the joint with the battery terminal in a lap sheer configuration relative to the interconnector busbar.

7. The method of claim 1, further comprising forming the joint with the battery terminal in a coach peel configuration relative to the interconnector busbar.

8. The method of claim 6, further comprising forming the joint with the interconnector busbar disposed between and configured in a coach peel configuration relative to first and second battery terminals.

9. The method of claim 1, further comprising forming the joint with two battery terminals connected to the interconnector busbar.

10. The method of claim 1, further comprising forming the joint with three battery terminals connected to the interconnector busbar.

11. The method of claim 1, further comprising forming the joint with the battery terminal ultrasonically welded to the interconnector busbar.

12. A method of evaluating a battery module, comprising:
applying a number of tension loads to a test coupon representing a joint of the battery module, the test coupon including a segment of a battery terminal connected to a segment of an interconnector busbar;
measuring a number of electrical resistance values across the segments of the test coupon in response to the number of tension loads applied; and
forming a plot between the electrical resistance values as a function of tension loads.

13. The method of claim 12, further comprising obtaining a beginning of life (BOL) tension load corresponding to the lowest electrical resistance measured.

14. The method of claim 13, further comprising subjecting the test coupon to a predetermined number of fatigue cycles and obtaining a tension load value at the end of the fatigue cycles as the end of life (EOL) tension load.

15. The method of claim 14, further comprising eliminating the test coupon as a potential candidate for a joint in the battery module if the EOL tension load is equal to or greater than a predetermined percentage of BOL tension load.

16. The method of claim 12, further comprising identifying based on the plot a particular tension load corresponding to a measured electrical resistance value.

17. The method of claim 12, further comprising forming the test coupon with the battery terminal in a coach peel configuration relative to the interconnector busbar.

18. The method of claim 17, further comprising forming the test coupon with the interconnector busbar disposed between and configured in a coach peel configuration relative to first and second battery terminals.

19. The method of claim 12, further comprising forming the test coupon with two or more battery terminals connected to the interconnector busbar.

20. A method of evaluating a battery module, comprising:
applying a number of tension loads to a test coupon representing a joint of the battery module, the test coupon including a segment of a battery terminal connected to a segment of an interconnector busbar, the number of tension loads being applied to a location of the test coupon different from one or more welds of the test coupon through which the segment of the battery terminal is connected to the segment of the interconnector busbar;
measuring a number of electrical resistance values across the segments of the test coupon in response to the number of tension loads applied;
forming a plot between the electrical resistance values as a function of tension loads; and
identifying based on the plot a particular tension load corresponding to a measured electrical resistance value.

* * * * *